US012635905B2

(12) United States Patent

Moschos et al.

(10) Patent No.: US 12,635,905 B2

(45) Date of Patent: *May 26, 2026

(54) EXHALED BREATH CONDENSATE COLLECTION DEVICE AND A KIT OF PARTS THEREFOR

(71) Applicant: PULMOBIOMED LTD, Newcastle upon Tyne (GB)

(72) Inventors: Sterghios A. Moschos, London (GB); Izzet Kale, London (GB)

(73) Assignee: Pulmobiomed Ltd., Newcastle-upon-Tyne (GB)

( * ) Notice: Subject to any disclaimer, the term of this patent is extended or adjusted under 35 U.S.C. 154(b) by 181 days.

This patent is subject to a terminal disclaimer.

(21) Appl. No.: 17/707,399

(22) Filed: Mar. 29, 2022

(65) Prior Publication Data

US 2022/0218229 A1    Jul. 14, 2022

Related U.S. Application Data

(63) Continuation of application No. 16/083,246, filed as application No. PCT/GB2017/050627 on Mar. 8, 2017, now Pat. No. 11,369,285.

(30) Foreign Application Priority Data

Mar. 8, 2016    (GB) ..................................... 1604011

(51) Int. Cl.
*A61B 5/097*        (2006.01)
*A61B 5/08*         (2006.01)
(Continued)

(52) U.S. Cl.
CPC ............. *A61B 5/097* (2013.01); *A61M 39/06* (2013.01); *A61M 39/22* (2013.01); *B01L 3/5021* (2013.01);
(Continued)

(58) Field of Classification Search
CPC . A61B 5/082; A61B 5/097; A61B 2010/0087; A61M 39/06; A61M 39/22
(Continued)

(56) References Cited

U.S. PATENT DOCUMENTS

2003/0208132 A1* 11/2003 Baddour ................ A61B 5/082
                                                                              600/532
2004/0162500 A1    8/2004 Kline
(Continued)

FOREIGN PATENT DOCUMENTS

CN        201289439 Y      8/2009
CN        102599913 A      7/2012
(Continued)

OTHER PUBLICATIONS

International Search Report from International Application No. PCT/GB2017/050627, mailed May 24, 2017, 6 pages.
(Continued)

*Primary Examiner* — Puya Agahi
(74) *Attorney, Agent, or Firm* — TraskBritt

(57)                ABSTRACT

A kit of parts for an exhaled breath condensate collection device. The kit comprises an assembly including a mouthpiece module. The kit further comprises a collection vessel configured to be cooled in use and configured for insertion into the assembly. The collection vessel defines a sealed and resealable chamber for collecting exhaled breath condensate in use. The collection vessel has a vessel breath inlet for admitting exhaled breath into the chamber. The kit of parts is configured such that the collection vessel is removable from the device in a sample containment configuration in which the collection vessel chamber is resealed. One or more parts of the kit of parts is configured and/or operable such that the collection vessel is caused to be resealed into the sample containment configuration after sample collec-
(Continued)

tion before the collection vessel is fully removed from the device.

25 Claims, 12 Drawing Sheets

(51) Int. Cl.

| | | |
|---|---|---|
| *A61B 10/00* | (2006.01) | |
| *A61M 39/06* | (2006.01) | |
| *A61M 39/22* | (2006.01) | |
| *B01L 3/00* | (2006.01) | |
| *B65D 47/26* | (2006.01) | |

(52) U.S. Cl.
CPC ....... *A61B 5/082* (2013.01); *A61B 2010/0087* (2013.01); *A61B 10/0096* (2013.01); *B65D 47/26* (2013.01)

(58) Field of Classification Search
USPC .......................... 600/529, 532, 538, 540, 543
See application file for complete search history.

(56) References Cited

U.S. PATENT DOCUMENTS

| | | | | |
|---|---|---|---|---|
| 2007/0203424 A1* | 8/2007 | Kline | ..................... | A61B 5/097 |
| | | | | 600/543 |
| 2008/0009761 A1 | 1/2008 | Acker et al. | | |
| 2010/0191138 A1 | 7/2010 | Bulbrook | | |
| 2010/0268106 A1* | 10/2010 | Johnson | ................. | B82Y 30/00 |
| | | | | 600/532 |
| 2010/0292601 A1* | 11/2010 | Dompeling | ............ | A61B 5/411 |
| | | | | 600/543 |
| 2012/0021375 A1 | 1/2012 | Binner et al. | | |
| 2012/0186328 A1 | 7/2012 | Makino et al. | | |
| 2012/0226183 A1 | 9/2012 | Christman et al. | | |
| 2013/0253360 A1* | 9/2013 | Wang | ................. | G01N 33/0047 |
| | | | | 600/532 |
| 2013/0253361 A1* | 9/2013 | Traficante | ............. | A61B 5/097 |
| | | | | 600/543 |
| 2014/0288454 A1* | 9/2014 | Paz | ...................... | A61B 5/4845 |
| | | | | 600/532 |
| 2016/0022946 A1* | 1/2016 | Sislian | ................... | A61B 10/00 |
| | | | | 600/543 |

FOREIGN PATENT DOCUMENTS

| | | | | |
|---|---|---|---|---|
| CN | 203955373 U | 11/2014 | | |
| EP | 1272245 A1 | 1/2003 | | |
| JP | 2010-534333 A | 11/2010 | | |
| JP | 2011-504235 A | 2/2011 | | |
| JP | 2012-163544 A | 8/2012 | | |
| WO | WO-9518566 A1 * | 7/1995 | ............ | A61B 5/097 |
| WO | 01/78819 A1 | 10/2001 | | |
| WO | WO-2007096649 A1 * | 8/2007 | ............ | A61B 5/097 |
| WO | 2009/066176 A2 | 5/2009 | | |
| WO | WO-2011018669 A2 * | 2/2011 | ............ | A61B 5/097 |

OTHER PUBLICATIONS

International Written Opinion from International Application No. PCT/GB2017/050627, mailed May 24, 2017, 9 pages.

* cited by examiner

EXHALED BREATH CONDENSATE COLLECTION DEVICE AND A KIT OF PARTS THEREFOR

CROSS-REFERENCE TO RELATED APPLICATIONS

This application is a continuation of U.S. patent application Ser. No. 16/083,246, filed Sep. 7, 2018, now U.S. Pat. No. 11,369,285, issued Jun. 26, 2022, which is a national phase entry under 35 U.S.C. § 371 of International Patent Application PCT/GB2017/050627, filed Mar. 8, 2017, designating the United States of America and published as International Patent Publication WO 2017/153755 A1 on Sep. 14, 2017, which claims the benefit under Article 8 of the Patent Cooperation Treaty to United Kingdom Application Serial No. 1604011.5, filed Mar. 8, 2016, the disclosure of each of which is hereby incorporated herein in its entirety by this reference.

TECHNICAL FIELD

The present disclosure relates to an exhaled breath condensate collection device, a kit of parts for the exhaled breath condensate collection device and a method of exhaled breath condensate collection.

BACKGROUND

Exhaled breath vapor typically contains a mixture of different components, which can give an indication of airway disease and physiology for a subject. It is known to extract these components by passing exhaled breath directly through a cooled collection vessel in order to initiate condensing of many of the constituent parts of the exhaled breath vapor. The exhaled breath condensate remains in the collection vessel, whilst any remaining vapor continues out of the collection vessel.

One of the known systems is described in U.S. Pat. No. 8,491,494, which discloses a mouthpiece connected to a collection vessel and a cooled aluminum sleeve useable to cool the collection vessel in use.

It is in this context that the present disclosure has been devised.

BRIEF SUMMARY

During development, it was realized that collected exhaled breath condensate using the device described in U.S. Pat. No. 8,491,494 is susceptible to contamination when the mouthpiece is removed from the collection vessel because a separate sealing cap is only applied to the collection vessel after removal of the mouthpiece. Between removal of the mouthpiece and application of the sealing cap, the collection vessel is open to the air. In this situation, contaminants may enter the collection vessel, possibly distorting the results of any subsequent analysis. Furthermore, the collection vessel may heat up between collection and sealing, resulting in evaporation of some of the collected exhaled breath condensate. Thus, some of the collected exhaled breath condensate sample may escape from the collection vessel.

In accordance with the present disclosure there is provided a kit of parts for an exhaled breath condensate collection device. The kit comprises a mouthpiece module comprising a breath passageway defined in the mouthpiece module providing fluid conduction from a mouthpiece breath inlet port for receiving exhaled breath to a mouthpiece breath outlet port in use. The kit further comprises a collection vessel for insertion into the device for cooling in use. The collection vessel defines a sealed and resealable chamber for collecting exhaled breath condensate in use. The collection vessel has a vessel breath inlet for admitting exhaled breath into the chamber. The kit of parts is configured such that the collection vessel is: insertable into the device into a sample collection configuration in which the vessel breath inlet is unsealed and in fluid communication with the mouthpiece breath outlet port of the mouthpiece module; and removable from the device in a sample containment configuration in which the collection vessel chamber is resealed. One or more parts of the kit of parts is configured and/or operable such that the collection vessel is caused to be resealed into the sample containment configuration after sample collection before the collection vessel is fully removed from the device.

Thus, contamination of the sample is substantially reduced by providing the collection vessel in a sealed configuration prior to insertion into the device, and resealing the collection vessel into the sample containment configuration after sample collection but before the collection vessel is fully removed from the device. This configuration also substantially prevents loss of the sample from the collection vessel.

One or more parts of the kit of parts may be configured and/or operable such that the collection vessel is caused to be unsealed into the sample collection configuration on or following insertion of the collection vessel into the device. Thus, the collection vessel is only unsealed on or following insertion of the collection vessel into the device, which substantially prevents contamination of the collection vessel from contaminants outside the device.

The mouthpiece module may be configured such that the mouthpiece breath outlet port is moveable to cause the vessel breath inlet to become unsealed on or following insertion of the collection vessel into the device. Thus, a simple mechanical movement is used to unseal the collection vessel.

The vessel breath inlet may be sealed by a film seal. The mouthpiece module may be configured such that the mouthpiece breath outlet port is moveable to penetrate the film on coupling of the mouthpiece breath outlet port in fluid communication with the vessel breath inlet.

The collection vessel may be caused to be unsealed into the sample collection configuration by a sliding seal. The collection vessel may be caused to be unsealed into the sample collection configuration by a rotary seal. The collection vessel may be caused to be unsealed into the sample collection configuration by a thermal seal. The collection vessel may be caused to be unsealed into the sample collection configuration by a pneumatic seal. The collection vessel may be caused to be unsealed into the sample collection configuration by a mechanical seal. The collection vessel may be caused to be unsealed into the sample collection configuration by an electromechanical seal. The collection vessel may be caused to be unsealed into the sample collection configuration by a chemical seal. The collection vessel may be caused to be unsealed into the sample collection configuration by a linear seal. The collection vessel may be caused to be unsealed into the sample collection configuration by a circular seal. The collection vessel may be caused to be unsealed into the sample collection configuration by a constricting seal. The collection vessel may be caused to be unsealed into the sample collection configuration by a spigot seal. The collection vessel may be caused to be unsealed into the sample collection configuration by a valve seal. The collection vessel may be caused to be unsealed into the sample collection configuration by a vacuum based seal.

The rotary seal may be an iris mechanism. The thermal seal may be a thermal sealing of plastics. The chemical seal may be a chemical glue seal. It will be appreciated that other sealing methods and mechanisms will be apparent to the person skilled in the art.

Additional sealing or resealing mechanisms may involve thermally activated seals, photochemically activated seals such as UV crosslinking or other compositive wavelength-reactive materials.

The collection vessel may further comprise a sealed vessel exhaust outlet to emit collected breath in use. The mouthpiece module may further comprise an exhaust passageway coupled to a mouthpiece exhaust inlet port to conduct exhausted breath away from the collection vessel in use. The mouthpiece exhaust inlet port may be moveable to cause the vessel exhaust outlet to become unsealed on or following insertion of the collection vessel into the device.

The vessel exhaust outlet may be sealed by a film seal. The mouthpiece exhaust inlet port may be moveable to penetrate the film on coupling of the mouthpiece exhaust inlet port in fluid communication with the vessel exhaust outlet.

The sealing methods described hereinbefore may be used to seal one or both of the vessel breath inlet and the vessel exhaust outlet.

The mouthpiece module may be formed such that the mouthpiece breath outlet port and mouthpiece exhaust inlet port are rigidly coupled to one or more moveable components. The mouthpiece module may be configured to be user-operable to cause the movement of the one or more moveable components to cause the collection vessel to become unsealed and in the sample collection configuration in use.

The device may comprise at least two manual, mechanical, electric or electronic sensors and/or switches that ensure proper alignment and locking of the mouthpiece module with the collection vessel upon insertion and/or initiation of the collection vessel through manual or housing-controlled electronic and/or mechanical actuation. The sensors and switches may be electromagnetic sensors and switches.

Basically, a system that uses electromagnetism to snap-on and snap-off the collector vessel and the mouthpiece module so that everything is appropriately aligned and held in place using just electromagnets.

The collection vessel may comprise a resealing mechanism configured to be caused to reseal the collection vessel as the collection vessel is removed from the device or at least from the part of the device in which the collection vessel is cooled in use.

The resealing mechanism may be one of the sealing methods or mechanisms hereinbefore described.

The collection vessel and one or more other parts of the device may be configured such that the resealing mechanism is configured to cooperate with the one or more other parts of the device to cause the collection vessel to be resealed.

The resealing mechanism may be biased toward a sealed configuration. The collection vessel and one or more other parts of the device may be configured to keep the resealing mechanism out of the sealed configuration when inserted into the device for sample collection and allow the resealing mechanism to return to the sealed configuration as the collection vessel is removed from the device. Thus, the collection vessel is sealed before being fully removed from the device, substantially preventing sample loss or contamination.

The resealing mechanism may comprise a sliding lid, which, when in the sealed configuration covers and seals at least the vessel breath inlet. The resealing mechanism may comprise a sliding lid, which, when in the sealed configuration covers and seals at least the vessel exhaust outlet.

The collection vessel and one or more other parts of the device may be configured such that the sliding lid of the resealing mechanism is urged open upon insertion into the device. The sliding lid of the resealing mechanism may be urged open by a lip of the lid that catches on the device.

The collection vessel and one or more other parts of the device may be configured such that the sliding lid of the resealing mechanism is urged shut upon removal from the device. The sliding lid of the resealing mechanism may be urged shut by a lip of the sliding lid that catches on the device.

A collection vessel housing of the kit may be configured for receiving the collection vessel for cooling during sample collection. The mouthpiece module may be configured to engage with the lip of the sliding lid to cause the device to be urged open and/or shut.

The sliding lid may abut in the mechanism against a resilient sealing material configured to seal the vessel when the lid is closed. The resilient sealing material may be a rubber material. The resilient sealing material may be neoprene. The resilient sealing material may be any other material able to withstand the range of temperatures specified for the device without loss of seal due to contraction or cracking. This may include elements, organic compounds or polymers used in isolation, combination, mixture, alloys or blends, where polymers might be homopolymers, heteropolymers, block co-polymers with linear, branched, dendrimeric, custom or chaotic structures used in isolation or combination with other inorganic and organic materials or compounds, manufactured by chemical synthesis, purification from natural or genetically engineered sources, through cell-free biological fabrication systems, molding, pressing, 3D printing or other means by which the necessary physicochemical properties can be achieved for the purpose of EBC collection.

The resealing mechanism may be configured such that the sliding lid is urged against the resilient sealing material to reinforce the seal if there is an overpressure inside the collection vessel.

The mouthpiece module may further comprise a seal configured to prevent air from flowing in the breath passageway at least through the mouthpiece breath inlet port when not in use. The seal may comprise a sealing member formed from a rubber material.

The kit of parts may further comprise a cooling component configured to cool the collection vessel to a temperature below minus 60 degrees Celsius. The cooling component may be configured to cool the collection vessel to a temperature of approximately minus 80 degrees Celsius. In some embodiments, the cooling component may be configured to cool the collection vessel to a temperature of between minus 80 degrees Celsius and 6 degrees Celsius. In some embodiments, the cooling component may be configured to control a temperature of the collection vessel to between minus 196 degrees Celsius and 20 degrees Celsius.

The mouthpiece module may further comprise a mouthpiece configured to be in fluid communication with the mouthpiece breath inlet port in use.

The mouthpiece module may further comprise a saliva trap between the mouthpiece breath inlet port and the mouthpiece breath outlet port.

The kit of parts may further comprise a mouthpiece temperature control component configured to maintain the mouthpiece module at a mouthpiece temperature of between 0 degrees Celsius and 46 degrees Celsius. The mouthpiece temperature may be an ambient temperature. The mouthpiece temperature may be a body temperature. The mouthpiece temperature may be substantially 37 degrees Celsius.

The kit of parts may further comprise a temperature sensor for the mouthpiece temperature control component or for the cooling component. The temperature sensor may be custom, integrated, off-the-shelf or chaotic structure, electronic, solid state, electromagnetic, optical, thermochromatic, or electric, with the option of sensor-centric and inter-sensor communication and processing capabilities in real time. There will be at least one temperature sensor but preferably more, standby, active redundant, located at uniform or non-uniform intervals and spacing in all components to enable reliable, high efficiency thermal regulation.

The kit of parts may comprise temperature control components configured to use advanced digital control and digital signal processing to maintain stable and controlled temperature during all phases of operation located in the non-disposable components of the device (housing).

Heating elements may be instantiated and located around or embedded within the entirety or parts of the housing of the disposable mouthpiece to maintain the temperature within the range specified hereinbefore through preset modes. The temperature may be maintained at an ambient temperature or at a temperature of breath on exhalation. The temperature of breath on exhalation may be measured in real-time through mouthpiece sensors or may be determined based on a user-input specification provided via a digital control interface.

Cooling elements for the disposable sample collection device may be located or embedded on a non-disposable digital processing unit housing (DPU). The digital processing unit may interface with a co-housed intelligent processing, control, data acquisition and storage unit with integrated user interface display and control unit.

The cooling elements surrounding the disposable unit or embedded within the DPU casing may consist of any one or more of the following:

The cooling elements may comprise plates, straight, flat, angled, geometrically organized, curved, flanged or finned with/without millimeter, micrometer or nanometer features such as tubes, channels pores, fins or other custom or chaotic designs that achieve high thermal conductivity through maximization of surface area, flow, conductivity or radiation that enables accelerated, high efficiency thermodynamic exchange.

The cooling elements may comprise coils, flat, curved, concentric, corkscrew, lateral, horizontal, vertical or inter-digitating achieving the same effects as in the preceding paragraph.

The cooling elements may comprise custom developed chaotic structures. The cooling elements may comprise fins or pins. The cooling elements may comprise any structure achieving maximum surface area coverage of the collection vessel and thermodynamic exchange ratio optimization.

The different components may rely on interference fit on entry at ambient temperature to enable easier electrical, mechanical, electromechanical or manual means collection vessel extraction from the non-disposable housing upon actuation completion.

The interface between electronic/electrically controlled components and a control unit or processing unit may be of a serial interface nature, typically USB (universal serial bus).

The collection vessel may be configured to be centrifuge resistant and shaped to cause exhaled breath condensate to collect at a bottom of the chamber during centrifuging.

The collection vessel may further comprise an extraction port for removal of the exhaled breath condensate from the collection vessel. The extraction port may be arranged at the location of the chamber at which the condensate collects during centrifuging.

The extraction port may be coupleable to a syringe or an inserted needle. The extraction port may comprise a low resistance needle-puncture site. The extraction port may comprise a pressure cap assembly. The extraction port may comprise a 'female' snap cap assembly. An overpressure in the collection vessel may cause the exhaled breath condensate collected adjacent the extraction port to be ejected from the collection vessel and into the syringe or the inserted needle. A 'male' coupling to the 'female' snap cap assembly may snap the extraction port to an open position to enable overpressure in the collection vessel to cause the exhaled breath condensate collected adjacent to the extraction port to be ejected from the collection vessel into further device. The further device may be a single or possibly multiple parallel or serially arranged closed analytical device, or an open analytical device, which may include a spraying device of portable or fixed nature. The dimensions of the coupling mechanism may accommodate at least one but possibly more fluidic coupling channels of fixed or variable dimensions. The fluidic coupling channels may be centimeter to micrometer fluidic coupling channels.

The present disclosure may extend to a mouthpiece module for use in the exhaled breath condensate collection device as described previously.

The present disclosure may extend to a collection vessel for use in the exhaled breath condensate collection device as described previously.

The present disclosure may extend to an exhaled breath condensate collection device as described previously.

Viewed from another aspect, the present disclosure provides a method of operating an exhaled breath condensate device as described previously. The method comprises: inserting the collection vessel into the device to be cooled and to cause the collection vessel to become unsealed and ready for sample collection; breathing into the mouthpiece module to conduct breath to the collection vessel to collect exhaled breath condensate therein; and removing the collection vessel from the device to cause the collection vessel to be resealed before the collection vessel is fully removed from the device.

The method may further comprise centrifuging the collection vessel to cause the exhaled breath condensate to collect at a bottom of the vessel. The method may further comprise extracting the collected exhaled breath condensate from the collection vessel through a port provided at the bottom of the collection vessel.

The present disclosure may extend to a computer-readable medium having computer-readable data representative of one or more parts of the kit of parts for an exhaled breath condensate collection device, or a mouthpiece module or a collection vessel, each as described previously, and useable by a 3D printer to print the one or more parts of the kit of parts.

BRIEF DESCRIPTION OF THE DRAWINGS

Embodiments of the present disclosure are further described hereinafter with reference to the accompanying drawings, in which.

DETAILED DESCRIPTION

Figure 1A:
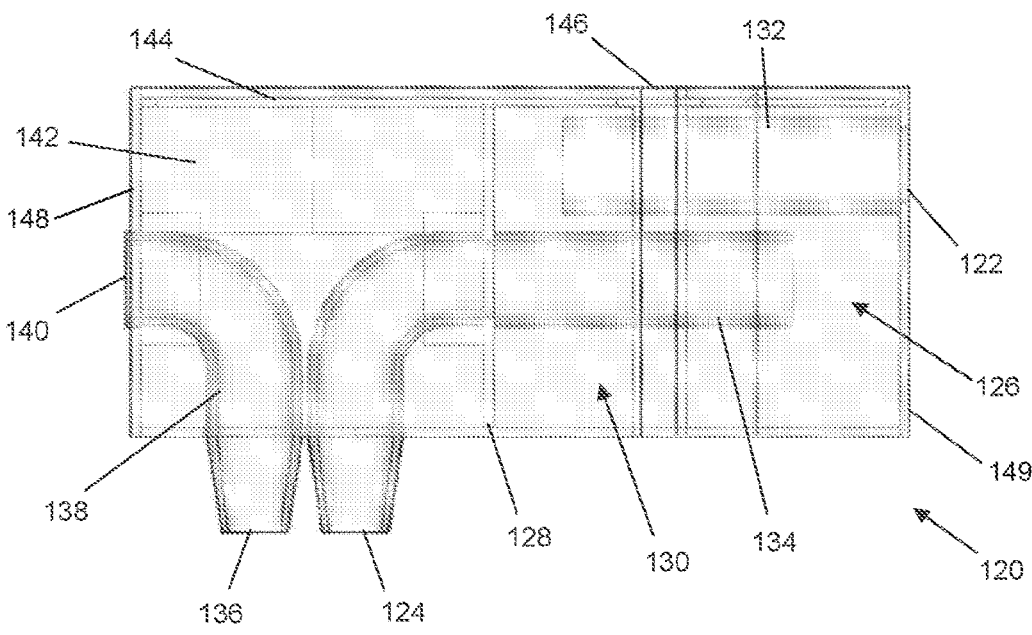
FIG. 1A is a diagram showing a mouthpiece inner component of a mouthpiece module in accordance with an embodiment of the present disclosure.
Figure 2A:
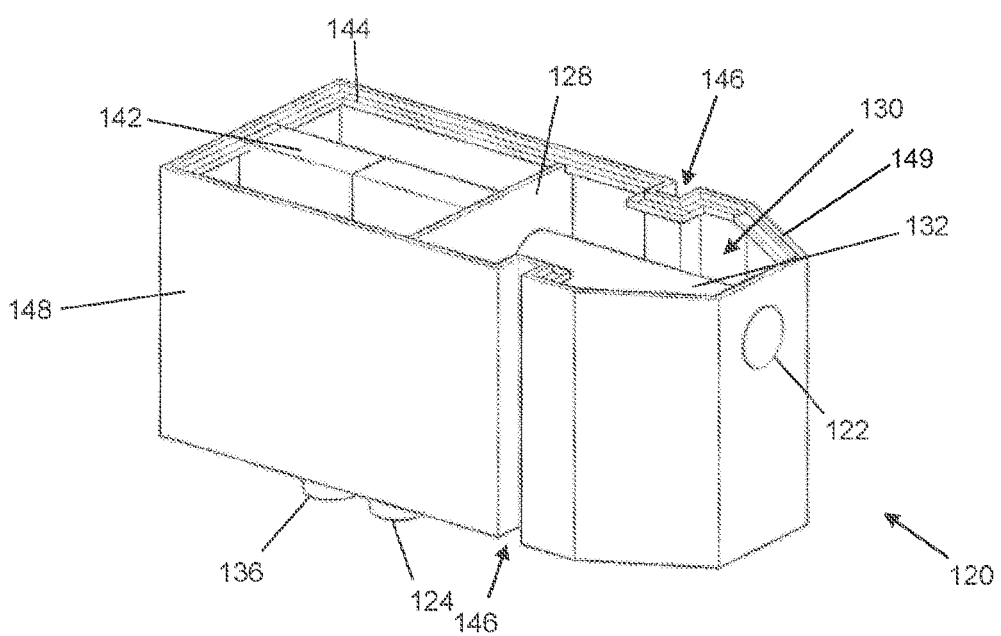
FIG. 2A is an isometric view of the mouthpiece inner component of FIG. 1A.

FIG. 1A is a diagram showing a mouthpiece inner component 120 of a mouthpiece module 100 in accordance with an embodiment of the present disclosure. FIG. 1A is provided in a semi-transparent view whereby to illustrate internal details of the mouthpiece inner component 120. FIG. 2A is an isometric view of the mouthpiece inner component 120 of FIG. 1A. FIG. 2A does not exhibit the same semi-transparent nature as FIG. 1A, whereby to more clearly illustrate the configuration of the mouthpiece inner component 120. The mouthpiece inner component 120 has defined therein a mouthpiece breath inlet port 122 configured to receive exhaled breath from a subject and a mouthpiece breath outlet port 124 arranged to be in fluid communication with the mouthpiece breath inlet port 122 to form a breath passageway and to output exhaled breath out of the mouthpiece module 100. The mouthpiece inner component 120 further comprises a saliva trap 126 in a mouthpiece first chamber 130 formed in the breath passageway between the mouthpiece breath inlet port 122 and the mouthpiece breath outlet port 124. A dividing member 128 divides the mouthpiece inner component 120 and defines a boundary of the mouthpiece first chamber 130. The mouthpiece first chamber 130 comprises a mouthpiece breath inlet tube 132, providing the mouthpiece breath inlet port 122 at an upstream end of the mouthpiece breath inlet tube 132. The mouthpiece first chamber 130 further comprises a mouthpiece breath outlet tube 134 providing a breath passageway from within the mouthpiece first chamber 130 to the mouthpiece breath outlet port 124 provided at a downstream end of the mouthpiece breath outlet tube 134. A region of the mouthpiece breath outlet tube 134 adjacent the mouthpiece breath outlet port 124 is shaped to have an inwardly tapered shape, whereby an area of the passageway through the mouthpiece breath outlet tube 134 reduces in a downstream direction. In this way, the mouthpiece breath outlet tube 134 provides a dibble at the downstream end. The mouthpiece inner component 120 further comprises a mouthpiece exhaust tube 138, being provided with a mouthpiece exhaust inlet port 136 at an upstream end and a mouthpiece exhaust outlet port 140 at a downstream end. The mouthpiece exhaust tube 138 is shaped to have an inwardly tapered shape, whereby an area of the passageway through the mouthpiece exhaust tube 138 reduces in an upstream direction. In this way, the mouthpiece exhaust tube 138 provides a dibble at the upstream end. The mouthpiece inner component 120 is provided in a shell 148 having holes defined therein to accommodate passage therethrough of the mouthpiece breath inlet port 122, mouthpiece breath outlet port 124, mouthpiece exhaust inlet port 136 and the mouthpiece exhaust outlet port 140. The shell 148 has defined therein at each side an elongate channel 146 running substantially parallel to the direction of the mouthpiece breath outlet tube 134 in the region of the mouthpiece breath outlet port 124. The shell 148 is further provided with a support flange 144 around an inner side of the periphery of the shell 148. A support member 142 may be referred to as a septum and is provided within the shell 148 to support the mouthpiece breath outlet tube 134 and the mouthpiece exhaust tube 138 in a deformed configuration whereby to ensure the mouthpiece exhaust inlet port 136 and the mouthpiece breath outlet port 124 are rigidly positioned even when pressure is applied against the mouthpiece exhaust inlet port 136 or the mouthpiece breath outlet port 124.

Figure 1B:
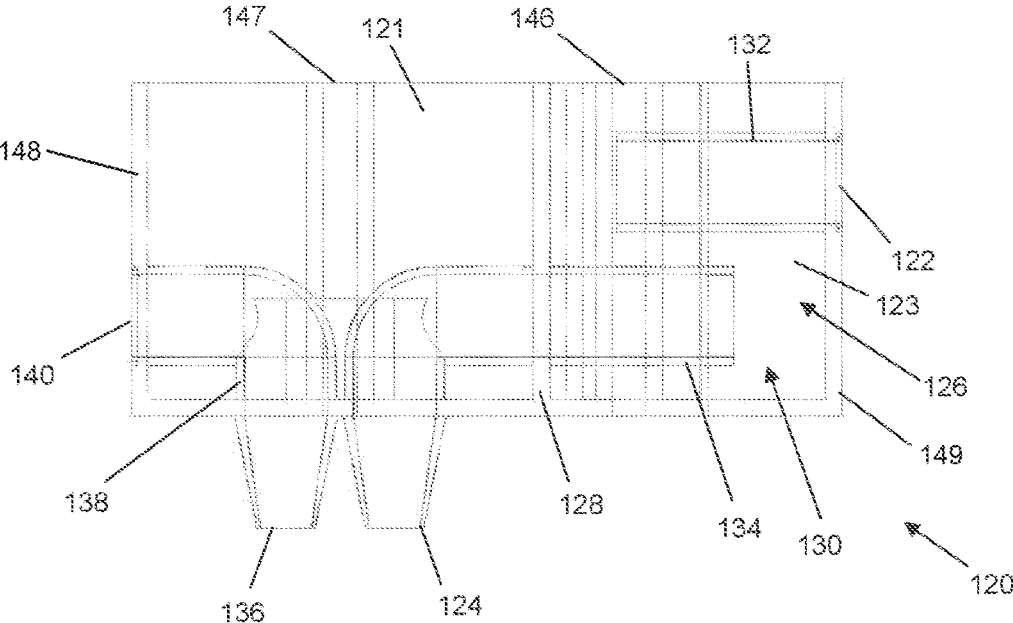
FIG. 1B is a diagram showing a mouthpiece inner component of a mouthpiece module in accordance with another embodiment of the present disclosure.
Figure 2B:
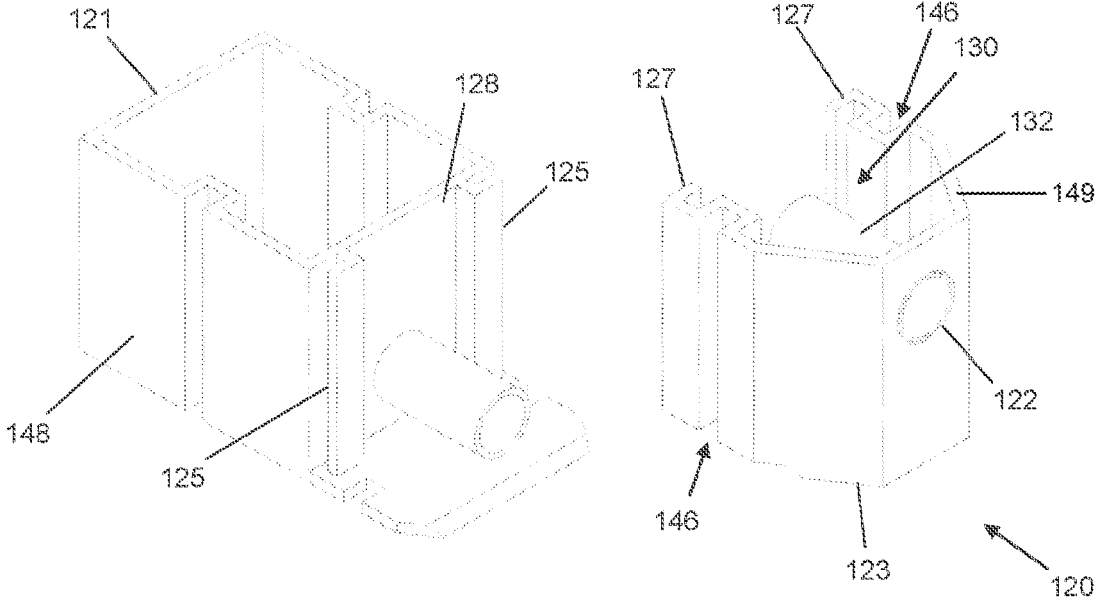
FIG. 2B is an isometric view of the mouthpiece inner component of FIG. 1B.

FIG. 1B is a diagram showing a mouthpiece inner component of a mouthpiece module being substantially similar to that shown in FIG. 1A apart from the hereinafter described differences. FIG. 2B is an isometric view of the mouthpiece inner component of FIG. 1B. A shell 148 comprises both a first elongate channel 146 and a second elongate channel 147 each running substantially parallel to the direction of the mouthpiece breath outlet tube 134 in the region of the mouthpiece breath outlet port 124. As can be seen in FIG. 2B, the mouthpiece inner component 120 comprises a first inner component 121 and a second inner component 123. The second inner component 123 comprises the first elongate channel 146, the mouthpiece breath inlet tube 132 and the second shell 149 defining the boundary of the mouthpiece first chamber 130. The second inner component 123 is removable from the first inner component 121 of the mouthpiece inner component 120 for cleaning of the saliva trap formed therein. The first inner component 121 further comprises two connection members 125 arranged to slidably engage with corresponding connection members 127 provided on the second inner component 123.

Figure 3:
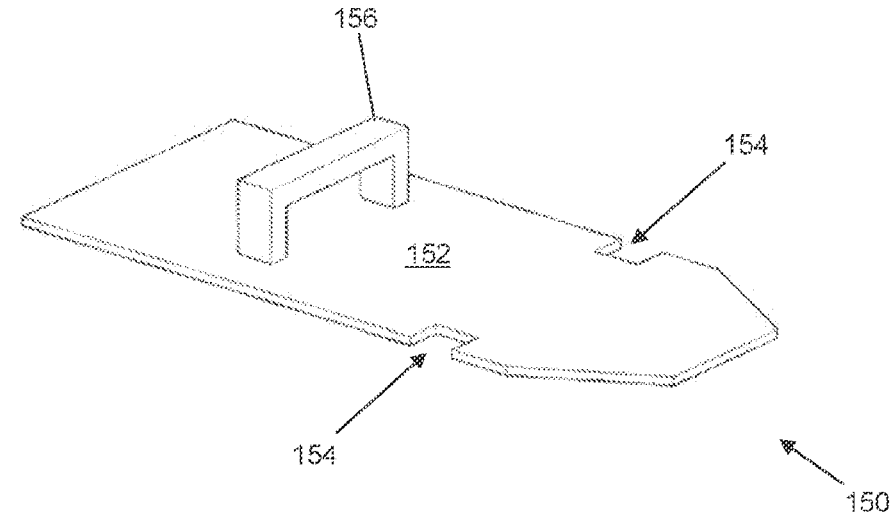
FIG. 3 is an isometric view of a lid for use with the mouthpiece inner component illustrated in FIGS. 1A and 2A.

FIG. 3 is an isometric view of a lid for use with the mouthpiece inner component illustrated in FIGS. 1A and 2A. The lid 150 comprises a planar lid member 152, shaped to close the mouthpiece inner component having a boundary shaped to interface with the support flange 144 of the mouthpiece inner component 120, in particular, having defined therein a recess 154 arranged to match the elongate channel 146 provided in the shell 148 of the mouthpiece inner component 120. The lid 150 further comprises a handle 156 extending from the planar lid member 152 and configured to allow the lid to be easily removed from the mouthpiece inner component 120.

Figure 4:
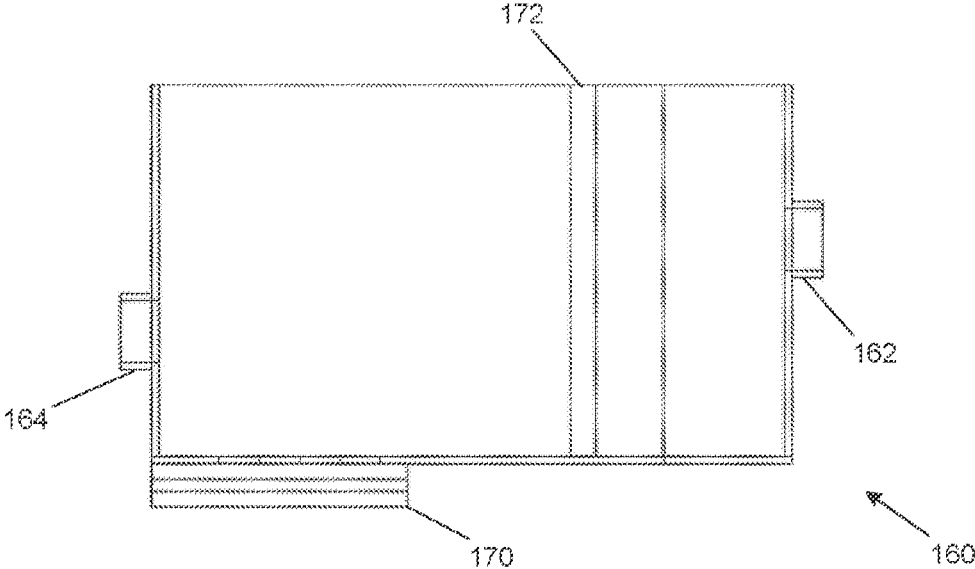
FIG. 4 is a diagram showing a mouthpiece housing component of a mouthpiece module in accordance with an embodiment of the present disclosure.
Figures 5, 6:
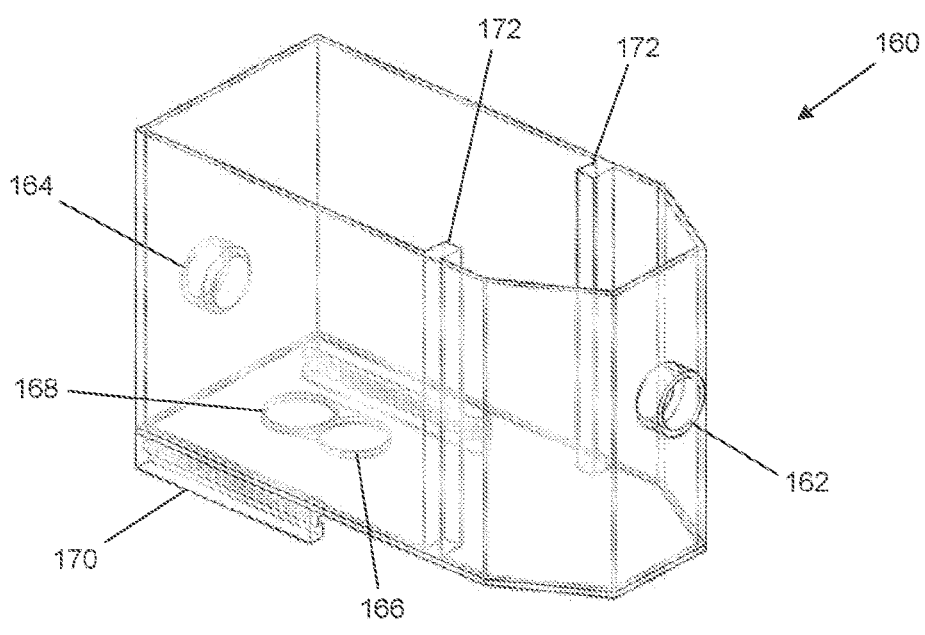
FIG. 5 is an isometric view of the mouthpiece housing component shown in FIG. 4.
FIG. 6 is a diagram of a collection vessel housing in accordance with an embodiment of the present disclosure.

FIG. 4 is a diagram showing a mouthpiece housing component 160 of a mouthpiece module in accordance with an embodiment of the present disclosure. FIG. 5 is an isometric view of the mouthpiece housing component 160 shown in FIG. 4. The mouthpiece housing component 160 provides a mouthpiece 162. It will be appreciated that the mouthpiece 162 could alternatively be provided by a separate component configured to be connected to the mouthpiece housing component 160. The mouthpiece housing component 160 further comprises a mouthpiece exhaust 164 through which exhaled breath can exit the device. The mouthpiece housing component 160 is further provided with a mouthpiece housing breath outlet port 166 and a mouthpiece housing exhaust inlet port 168 on a lower surface of the mouthpiece housing component 160. A connection member in the form of a recess connection member 170 is provided to enable connection of the mouthpiece housing component 160 to a further component. An internal surface of the mouthpiece housing component 160 is provided with an internal protrusion 172 on each side of the mouthpiece housing component 160, whereby to interface with the elongate channel 146 formed in the mouthpiece inner component 120 when the mouthpiece inner component 120 is inserted within the mouthpiece housing component 160 as will be discussed further hereinafter. The mouthpiece housing component 160 further comprises a film seal (not shown) arranged to extend across the mouthpiece housing breath outlet port 166 and the mouthpiece housing exhaust inlet port 168.

Figure 7:
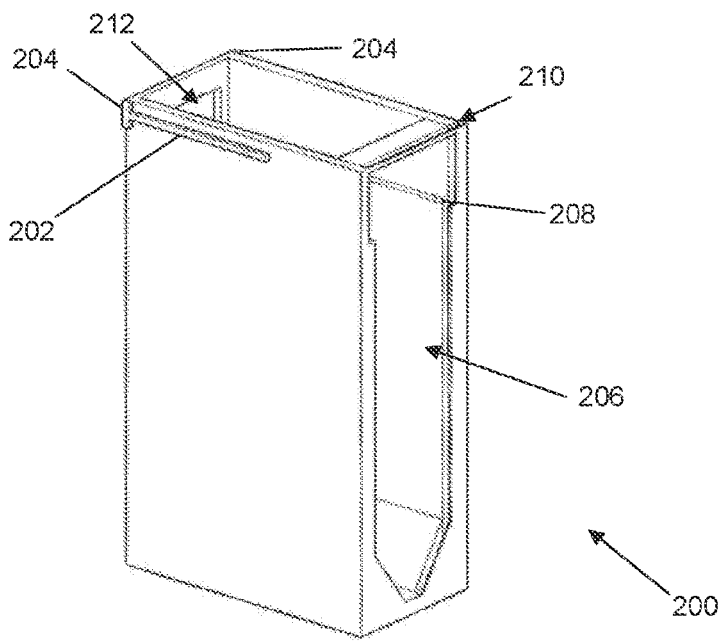
FIG. 7 is an isometric view of the collection vessel housing shown in FIG. 6.

FIG. 6 is a diagram of a collection vessel housing 200 in accordance with an embodiment of the present disclosure. FIG. 7 is an isometric view of the collection vessel housing 200 shown in FIG. 6. The collection vessel housing 200 comprises a connection member in the form of a collection vessel housing connecting protrusion 202 and an end stop 204 arranged to connect the collection vessel housing 200 to the mouthpiece housing component 160. The collection vessel housing 200 has defined therein a collection vessel receiving opening 206 provided in a side of the collection vessel housing 200 for insertion and removal of a collection vessel into the collection vessel housing 200. The collection vessel housing 200 is further provided with an internal flange 208 arranged to support the collection vessel and an opposing opening 212 provided opposite the collection vessel receiving opening 206 whereby to aid removal of the collection vessel from the collection vessel housing 200. The collection vessel housing 200 is also provided with a collection vessel housing engagement spacing whereby to operate a function of the collection vessel. The operation of the device and structure of the collection vessel will be described in more detail below.

Although not shown, the collection vessel housing 200 may further comprise a temperature control component configured to control a temperature of a collection vessel inserted into the collection vessel housing 200. The temperature control component may be a cooling component configured to actively cool the collection vessel. Alternatively, the temperature control component may be a heating component. Typically, during sample collection, the collection vessel housing 200 may be configured to cool the collection vessel to a temperature of −80 degrees Celsius. The cooling may be achieved using a Peltier, solid state, or electronic cooling element. As desirable, the temperature of the collection vessel may be controlled to be any temperature from minus 196 degrees Celsius to 20 degrees Celsius.

Furthermore, either or both of the mouthpiece housing component 160 and the mouthpiece inner component 120 may further comprise a mouthpiece temperature control component. The mouthpiece temperature control component may be a mouthpiece heating component or a mouthpiece cooling component. The mouthpiece temperature control component may be configured to control a temperature of the mouthpiece module 100 during collection of between 0 degrees Celsius to 46 degrees Celsius, though typically the temperature of the mouthpiece module 100 is desirably controlled to be at an ambient temperature.

It will be appreciated that any suitable method or mechanism for controlling the temperature of either or both of the collection vessel and the mouthpiece module may be used. For example, the temperature control may be achieved by electronic, electrical, chemical, physical, convectional, immersive, hydraulic, liquid, Peltier, solid state or mechanical temperature control mechanisms or methods.

Figure 8A:
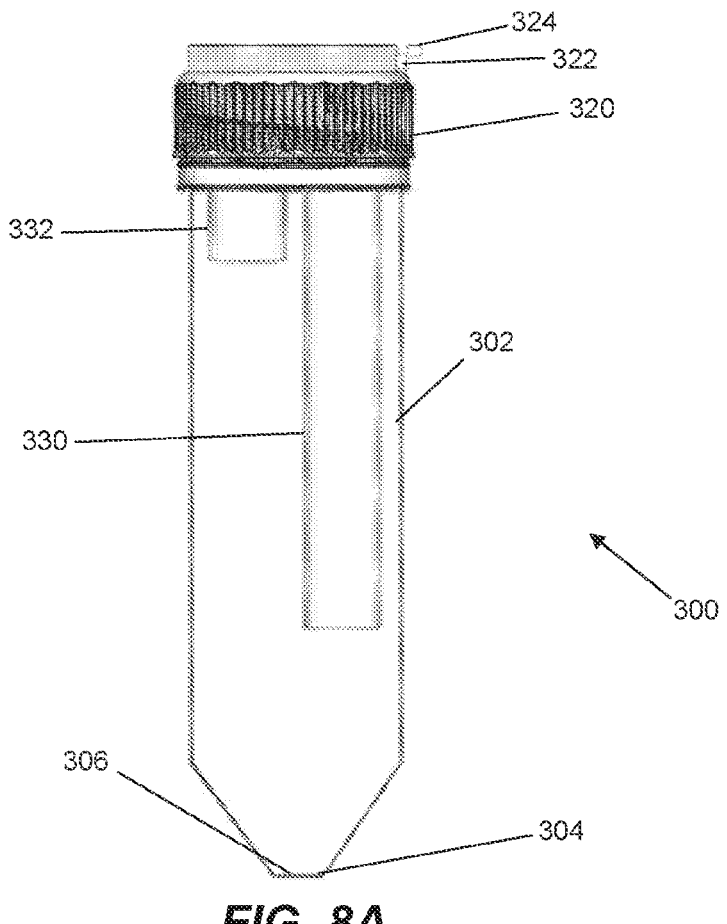
FIG. 8A is a diagram of a collection vessel in accordance with an embodiment of the present disclosure.
Figure 9A:
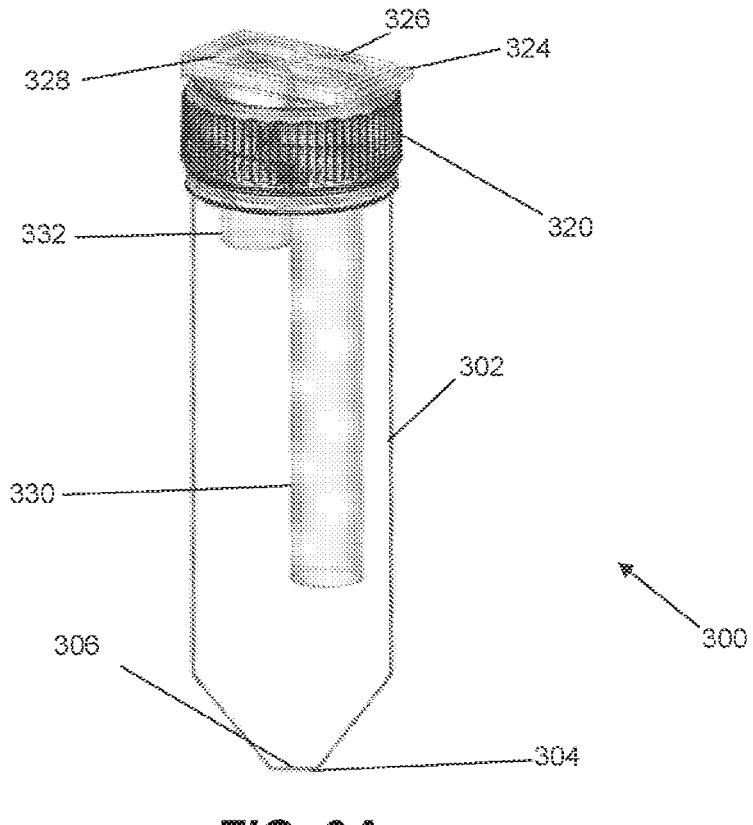
FIG. 9A is an isometric view of the collection vessel shown in FIG. 8A.

FIG. 8A is a diagram of a collection vessel 300 in accordance with an embodiment of the present disclosure. FIG. 9A is an isometric view of the collection vessel 300 shown in FIG. 8A. The collection vessel 300 comprises a phial 302 having a bottom 304 and a cap 320 on an uppermost portion of the phial 302. The collection vessel 300 further comprises a collection vessel extraction port 306 provided near the bottom 304 of the phial 302 and configured to be useable to remove collected condensate from the phial 302 for analysis. The cap 320 comprises a sealing mechanism in the form of a sliding lid 322 arranged to seal a vessel breath inlet 326 and a vessel exhaust outlet 328 when the lid is closed. The sliding lid 322 is provided with a lip 324 at an end of the sliding lid 322 operable to move the sliding lid 322 into or out of position. When the sliding lid 322 is open, the vessel breath inlet 326 and the vessel exhaust outlet 328 are accessible. In a sealed configuration, the collection vessel further comprises a seal in the form of a film (not shown) which covers the vessel breath inlet 326 and the vessel exhaust outlet 328 whereby to seal the collection vessel 300, even when the sliding lid 322 is open. The vessel breath inlet 326 is provided at an end of a vessel breath tube 330, which extends within the phial 302. The vessel exhaust outlet 328 is provided at an end of a vessel exhaust tube 332, which extends within the phial 302. The vessel breath tube 330 is longer than the vessel exhaust tube 332. The cap 320 is configured to connect to the phial 302 by a screw connection.

Figure 8B:
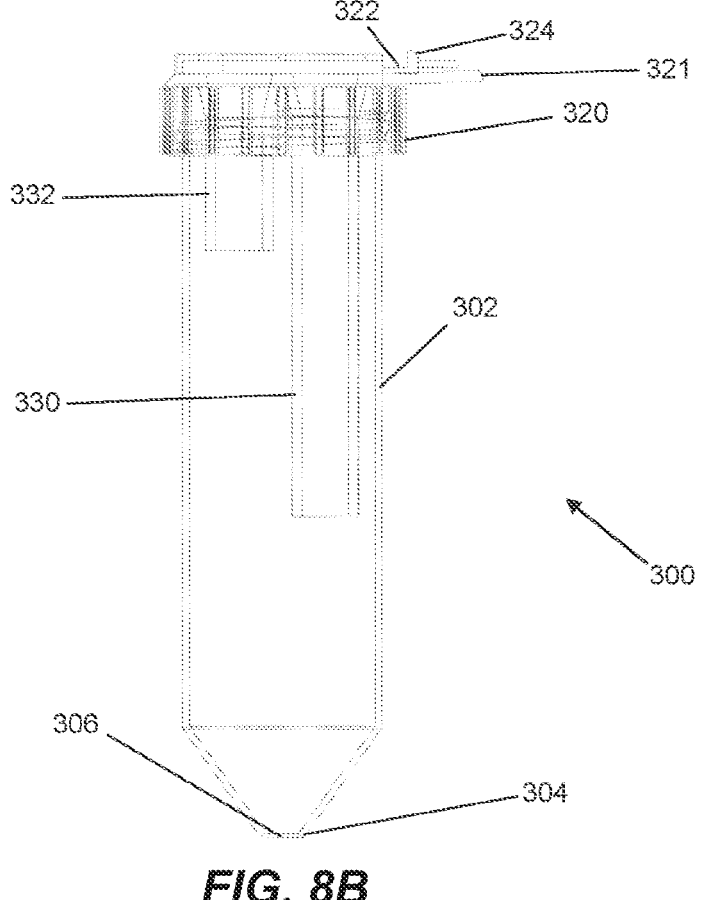
FIG. 8B is a diagram of a collection vessel in accordance with another embodiment of the present disclosure.
Figure 9B:
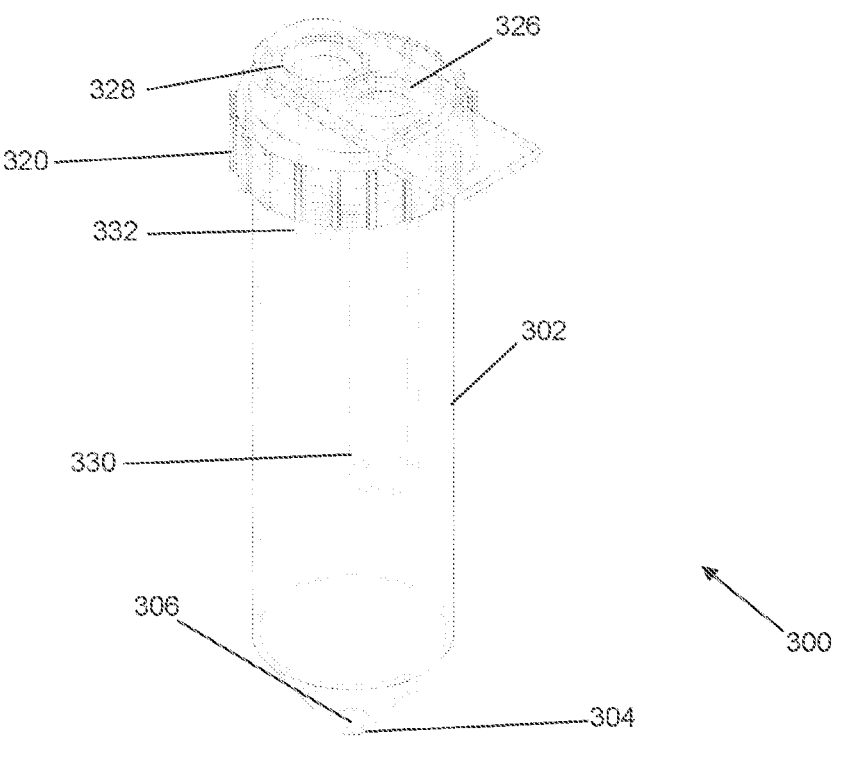
FIG. 9B is an isometric view of the collection vessel shown in FIG. 8B.

FIG. 8B is a diagram of a collection vessel being substantially similar to that shown in FIG. 8A apart from the hereinafter described differences. FIG. 9B is an isometric view of the collection vessel shown in FIG. 8B without the sliding lid 322. The cap 320 comprises an inclined shelf 321 arranged to engage with the sliding lid 322 and resist unsealing of the collection vessel 300 by free movement of the sliding lid 322 out of the recess provided in the cap 320. In comparison with FIG. 9A, FIG. 9B does not show a sliding lid 322 to better show the internal structure of the cap 320.

Figure 10:
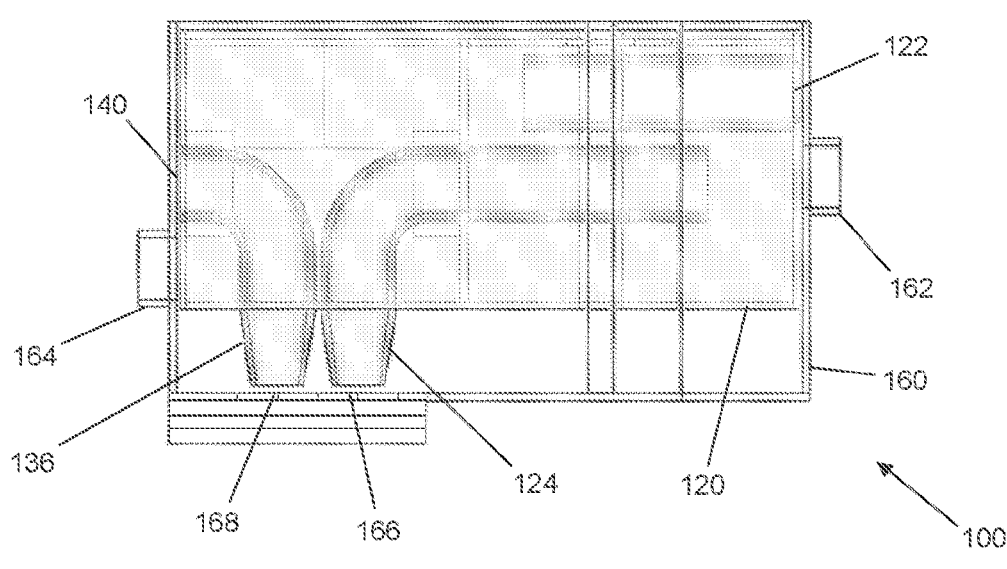
FIG. 10 is a diagram of the mouthpiece module formed by the assembly of the mouthpiece inner component shown in FIGS. 1A and 2A with the mouthpiece housing component shown in FIGS. 4 and 5, the mouthpiece module being shown in a sealed configuration.

FIG. 10 is a diagram of the mouthpiece module 100 formed by the assembly of the mouthpiece inner component 120 shown in FIGS. 1A and 2A with the mouthpiece housing component 160 shown in FIGS. 4 and 5, the mouthpiece module being shown in a sealed configuration. The mouthpiece inner component 120 is inserted within the mouthpiece housing component 160. In this first, sealed configuration, the mouthpiece breath outlet port 124 and the mouthpiece exhaust inlet port 136 of the mouthpiece inner component 120 do not extend through the mouthpiece housing breath outlet port 166 and the mouthpiece housing exhaust inlet port 168, such that the film seal remains intact. Furthermore, the mouthpiece breath inlet port 122 and the mouthpiece exhaust outlet port 140 are not aligned with the mouthpiece 162 and the mouthpiece exhaust 164, respectively. In this way, in the sealed configuration, there does not exist a breath passageway from the mouthpiece 162 to the mouthpiece housing breath outlet port 166 or from the mouthpiece housing exhaust inlet port 168 to the mouthpiece exhaust 164 and the mouthpiece module 100 can be considered to be sealed. Although not shown, it will be appreciated that the lid 150 is also provided on the mouthpiece inner component 120 to seal the mouthpiece module.

Figure 11:
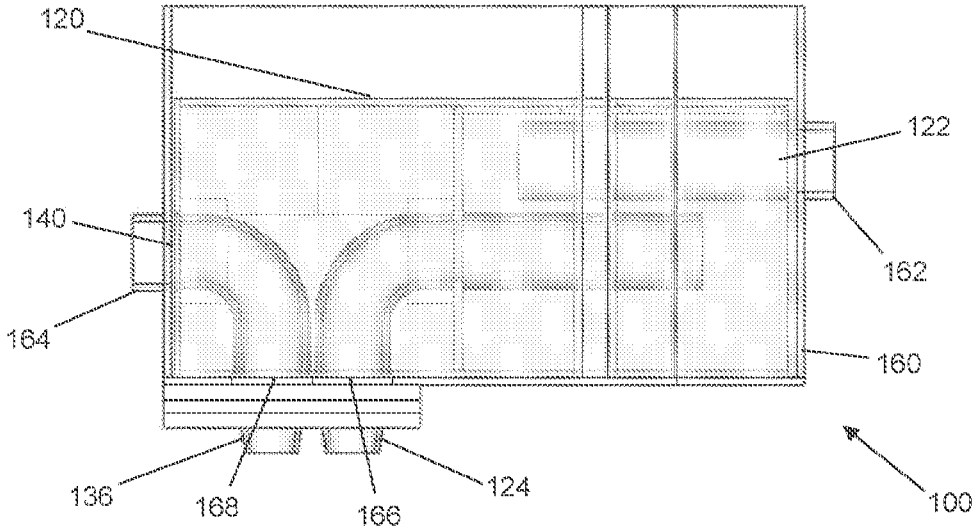
FIG. 11 is a diagram of the mouthpiece module of FIG. 10, shown in a sample collection configuration.

FIG. 11 is a diagram of the mouthpiece module of FIG. 10, shown in a sample collection configuration. In contrast with the configuration shown in FIG. 10, the mouthpiece inner component 120 is fully seated within the mouthpiece housing component 160. In this position, the dibbles formed by the mouthpiece breath outlet port 124 and the mouthpiece exhaust inlet port 136 puncture though the film seal and extend through the mouthpiece housing breath outlet port 166 and the mouthpiece housing exhaust inlet port 168. Furthermore, the mouthpiece breath inlet port 122 and the mouthpiece exhaust outlet port 140 are aligned with the mouthpiece 162 and the mouthpiece exhaust 164, respectively. In this way, in the sample collection configuration, there exists a breath passageway from the mouthpiece 162 to the mouthpiece housing breath outlet port 166 and from the mouthpiece housing exhaust inlet port 168 to the mouthpiece exhaust 164 and the mouthpiece module 100 can be considered to be unsealed. As in FIG. 10, it will be appreciated that the lid 150 is also provided on the mouthpiece inner component 120 to substantially prevent contamination of a breath sample.

Figure 12:
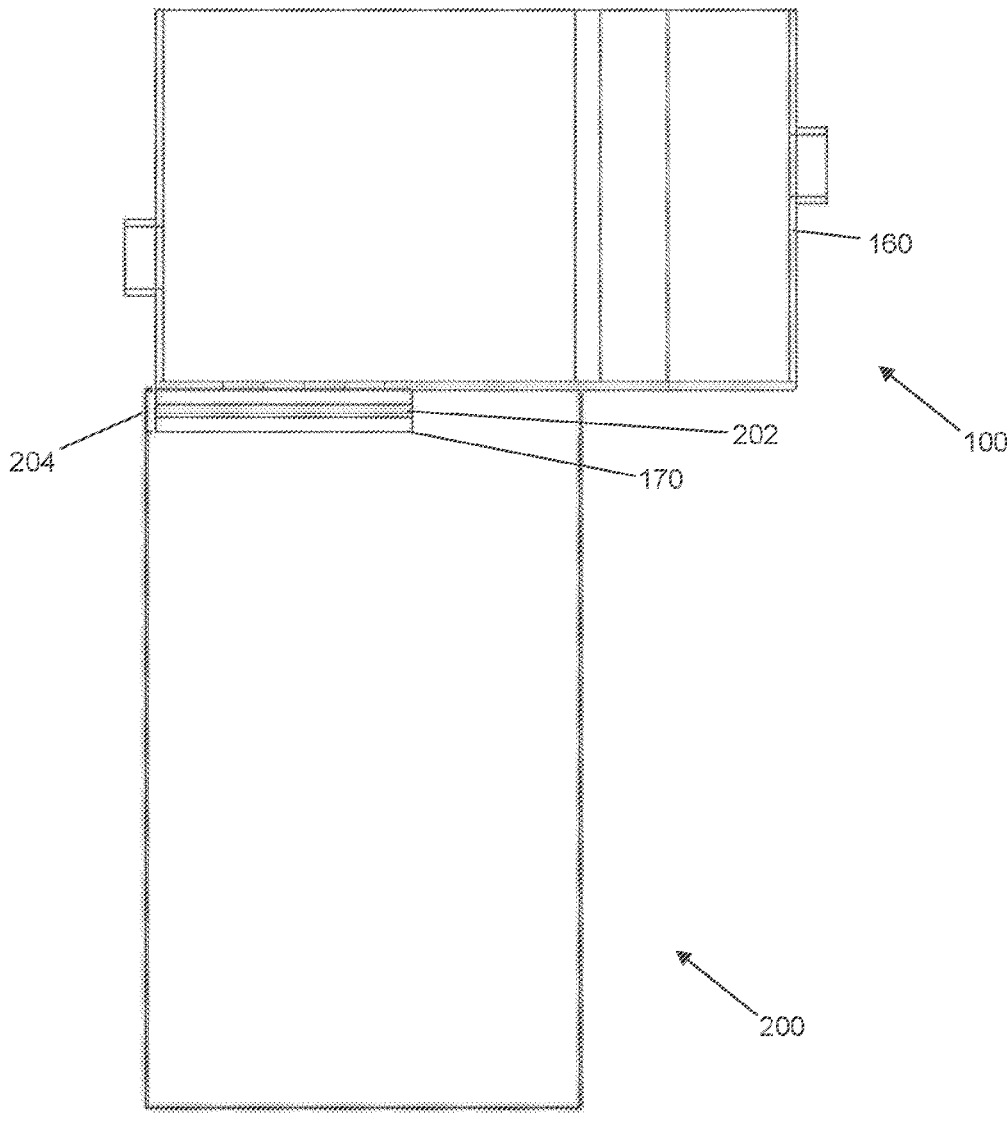
FIG. 12 is a diagram showing the mouthpiece module of FIGS. 10 and 11 assembled with the collection vessel housing shown in FIGS. 6 and 7.

FIG. 12 is a diagram showing the mouthpiece module of FIGS. 10 and 11 assembled with the collection vessel housing shown in FIGS. 6 and 7. The collection vessel housing 200 is mounted to the mouthpiece module 100 by sliding the collection vessel housing connecting protrusion 202 on each side of the collection vessel housing 200 into the two recess connection members 170 extending past a bottom surface of the mouthpiece housing component 160 until the end stop 204 is abutted against the recess connection member 170. The collection vessel housing 200 is typically attached to the mouthpiece module 100 whilst the mouthpiece is in the sealed configuration described in relation to FIG. 10 previously.

Figure 13:
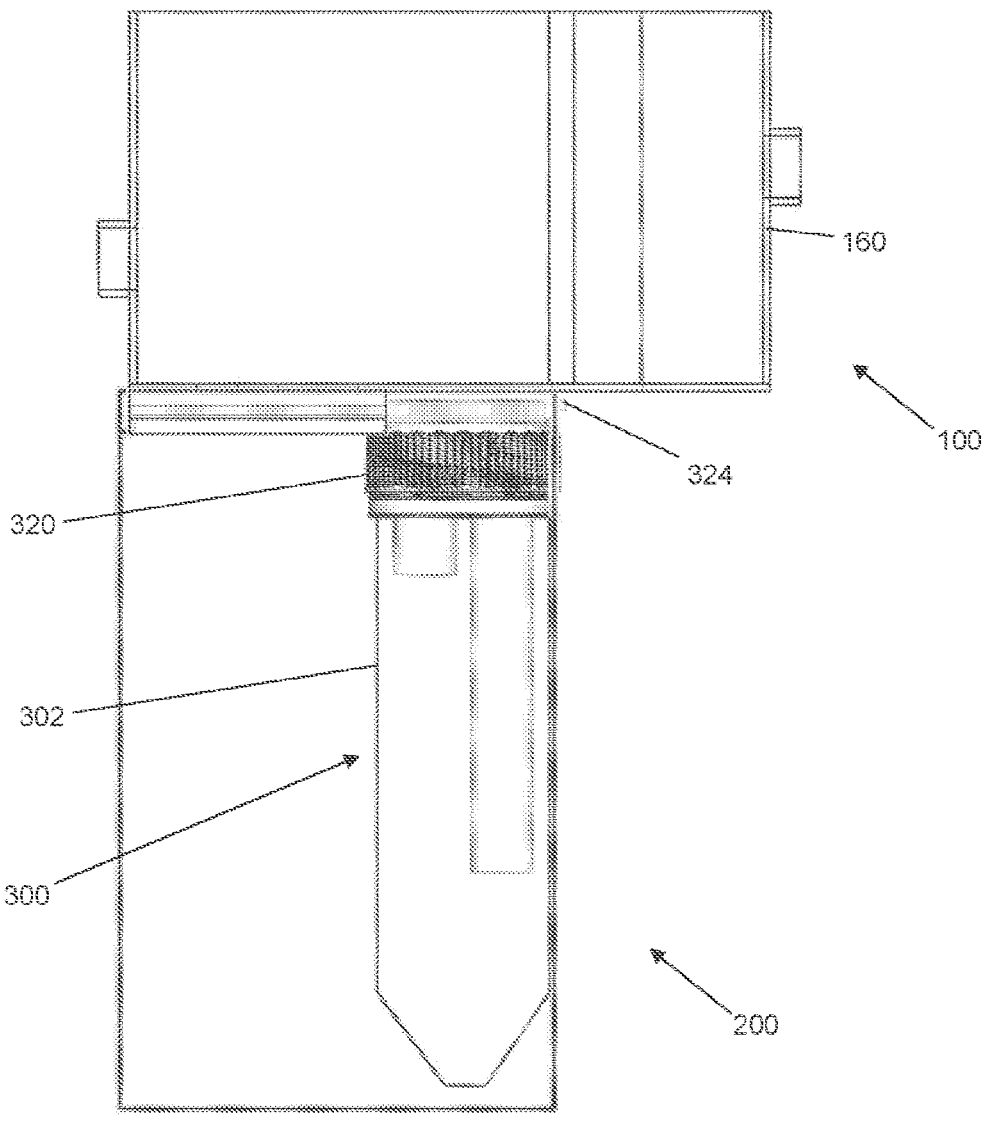
FIG. 13 is a diagram showing the assembly of FIG. 12 additionally comprising the collection vessel shown in FIGS. 8A and 9A.
Figure 14:
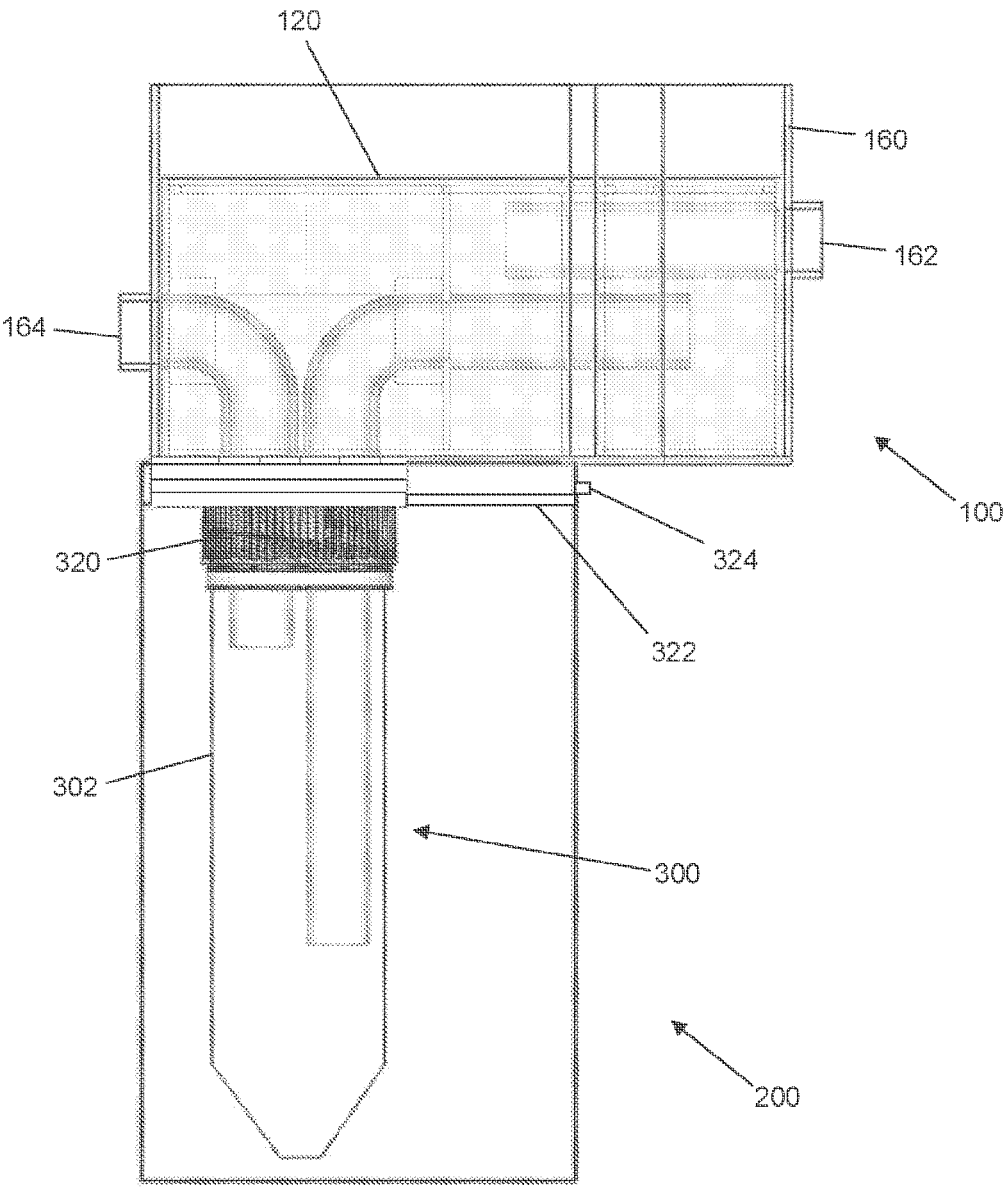
FIG. 14 is a diagram showing the assembly of FIG. 13 in a sample collection configuration.

FIG. 13 is a diagram showing the assembly of FIG. 12 additionally comprising the collection vessel shown in FIGS. 8A and 9A. The collection vessel 300 is inserted into the collection vessel housing 200 through the collection vessel receiving opening 206. The cap 320 of the collection vessel 300 is wider than the phial 302, so the cap slides over the internal flange 208 provided within the collection vessel housing 200. The lip 324 on the sliding lid 322 is configured to engage with the collection vessel housing engagement spacing 210 on insertion of the collection vessel 300 into the collection vessel housing 200. FIG. 14 is a diagram showing the assembly of FIG. 13 in a sample collection configuration. As the collection vessel 300 is fully inserted into the collection vessel housing 200, the lip 324 acts to withdraw the sliding lid 322 whereby to expose the sealing film (not shown) covering the openings of the vessel breath inlet 326 and the vessel exhaust outlet 328. Once the collection vessel 300 is fully inserted into the collection vessel housing 200, the mouthpiece module is converted into the sample collection configuration by depressing the mouthpiece inner component 120 fully within the mouthpiece housing component 160, whereby to cause the dibbles formed by the mouthpiece breath outlet port 124 and the mouthpiece exhaust inlet port 136 to pierce the sealing film and provide a breath passageway from the mouthpiece 162 to the mouthpiece exhaust 164 via the collection vessel 300.

When sample collection is completed, the mouthpiece module 100 is reconfigured by raising the mouthpiece inner component 120 within the mouthpiece housing component 160 whereby to substantially prevent contamination of the collection vessel 300. The collection vessel 300 is removed from the collection vessel housing 200 by pushing the collection vessel 300 through the opposing opening 212 provided in the collection vessel housing 200. As the collection vessel 300 slides out of the collection vessel housing 200, the collection vessel housing engagement spacing acts to operate on the lip 324 of the sliding lid 322 on the collection vessel 300, causing the sliding lid 322 to close, thereby sealing the collection vessel 300. In this way, the collection vessel 300 is provided in a fully sealed configuration before the collection vessel 300 is fully removed from the collection vessel housing 200, substantially preventing contamination of the collection vessel 300. The cap 320 of the collection vessel 300 comprises a resilient sealing member in the form of a rubber seal (not shown), whereby to provide a reliable seal for the collection vessel 300. Even when the pressure within the collection vessel 300 increased, the collection vessel 300 remains sealed. Typically, when the collection vessel 300 is removed from the cooled environment within the collection vessel housing 200, the temperature of the collection vessel will increase, therefore increasing the pressure within the collection vessel 300.

The collection vessel extraction port 306 provided on the bottom of the phial 302 of the collection vessel 300 allows condensate to be removed from the collection vessel 300. In one embodiment, the collection vessel 300 is first centrifuged to collect all of the condensate at an end of the collection vessel 300 adjacent the collection vessel extraction port 306. An overpressure within the collection vessel 300 acts to push the condensate out through the collection vessel extraction port 306 when it is desired to empty the collection vessel 300 for analysis.

In summary, there is provided a kit of parts for an exhaled breath condensate collection device. The kit comprises a mouthpiece module (100) comprising a breath passageway defined in the mouthpiece module (100) providing fluid conduction from a mouthpiece breath inlet port (122) for receiving exhaled breath to a mouthpiece breath outlet port (124) in use. The kit further comprises a collection vessel (300) for insertion into the device for cooling in use. The collection vessel (300) defines a sealed and resealable chamber for collecting exhaled breath condensate in use. The collection vessel has a vessel breath inlet (326) for admitting exhaled breath into the chamber. The kit of parts is configured such that the collection vessel (300) is: insertable into the device into a sample collection configuration in which the vessel breath inlet (326) is unsealed and in fluid communication with the mouthpiece breath outlet port (124) of the mouthpiece module (100); and removable from the device in a sample containment configuration in which the collection vessel chamber is resealed. One or more parts of the kit of parts is configured and/or operable such that the collection vessel (300) is caused to be resealed into the sample containment configuration after sample collection before the collection vessel (300) is fully removed from the device.

Throughout the description and claims of this specification, the words "comprise" and "contain" and variations of them mean "including but not limited to," and they are not intended to (and do not) exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers or characteristics described in conjunction with a particular aspect, embodiment or example of the present disclosure are to be understood to be applicable to any other aspect, embodiment or example described herein unless incompatible therewith.

All of the features disclosed in this specification (including any accompanying claims, abstract and drawings), and/or all of the steps of any method or process so disclosed, may be combined in any combination, except combinations where at least some of such features and/or steps are mutually exclusive. The present disclosure is not restricted to the details of any foregoing embodiments. The present disclosure is as defined in the appended claims.

The invention claimed is:

1. A kit of parts for an exhaled breath condensate collection device, the kit comprising:
   a mouthpiece module comprising a breath passageway defined in the mouthpiece module providing fluid communication from a mouthpiece breath inlet port for receiving exhaled breath to a mouthpiece breath outlet port in use; and
   a collection vessel configured to be cooled in use, the collection vessel defining a chamber for collecting exhaled breath condensate in use, wherein the chamber comprises a sealable and resealable vessel breath inlet for admitting exhaled breath into the chamber in use, wherein the vessel breath inlet is sealed prior to preparation for use, and wherein the collection vessel comprises a resealing mechanism configured to reseal the collection vessel;
   the kit of parts being configured for combination into an assembly comprising a sample collection configuration in which the collection vessel is inserted into the assembly and the vessel breath inlet of the collection vessel is unsealed and allows fluid communication with the mouthpiece breath outlet port of the mouthpiece module; and a sample containment configuration in which the chamber of the collection vessel is resealed and removed in a sealed configuration from the assembly;
   wherein one or more parts of the kit of parts separately or together cause the resealing mechanism to reseal the collection vessel in the sample containment configuration after sample collection before the collection vessel is fully removed from the assembly.

2. The kit of claim 1, wherein one or more parts of the kit of parts is configured and/or operable such that the collection vessel is caused to be unsealed into the sample collection configuration on or following insertion of the collection vessel into the assembly.

3. The kit of claim 1, wherein the mouthpiece module is configured such that the mouthpiece breath outlet port is moveable to cause the vessel breath inlet to become unsealed on or following insertion of the collection vessel into the assembly.

4. The kit of claim 1, wherein the vessel breath inlet is sealed by a film seal and wherein the mouthpiece module is configured such that the mouthpiece breath outlet port is moveable to penetrate the film seal on coupling of the mouthpiece breath outlet port in fluid communication with the vessel breath inlet.

5. The kit of claim 1, wherein the collection vessel further comprises a sealed vessel exhaust outlet to emit collected breath in use, wherein the vessel exhaust outlet is sealed, and wherein the mouthpiece module further comprises an exhaust passageway coupled to a mouthpiece exhaust inlet port to conduct exhausted breath away from the collection vessel in use, and wherein the mouthpiece exhaust inlet port is moveable to cause the vessel exhaust outlet to become unsealed on or following insertion of the collection vessel into the assembly.

6. The kit of claim 5, wherein the vessel exhaust outlet is sealed by a film seal and wherein the mouthpiece exhaust inlet port is moveable to penetrate the film seal on coupling of the mouthpiece exhaust inlet port in fluid communication with the vessel exhaust outlet.

7. The kit of claim 1, wherein the mouthpiece module is formed such that the mouthpiece breath outlet port and mouthpiece exhaust inlet port are rigidly coupled to one or more moveable components, and wherein the mouthpiece module is configured to be user-operable to cause movement of the one or more moveable components to cause the collection vessel to become unsealed and in the sample collection configuration when in use.

8. The kit of claim 1, in which the collection vessel and one or more other parts of the assembly are configured such that the resealing mechanism is configured to cooperate with the one or more other parts of the assembly to cause the collection vessel to be resealed.

9. The kit of claim 1, wherein the resealing mechanism comprises a sliding lid, which covers and seals at least the vessel breath inlet when the resealing mechanism is in a sample containment configuration.

10. The kit of claim 9, wherein the collection vessel and one or more other parts of the assembly are configured such that the sliding lid of the resealing mechanism is urged open upon insertion into the assembly.

11. The kit of claim 9, wherein the collection vessel and one or more other parts of the assembly are configured such that the sliding lid of the resealing mechanism is urged shut upon removal from the assembly.

12. The kit of claim 9, wherein a collection vessel housing configured for receiving the collection vessel for cooling during sample collection or the mouthpiece module is configured to engage with a lip of the sliding lid to cause the sliding lid to be urged open and/or shut.

13. The kit of claim 9, wherein the sliding lid abuts in the resealing mechanism against a resilient sealing material configured to seal the collection vessel when the sliding lid is closed.

14. The kit of claim 13, wherein the resealing mechanism is configured such that the sliding lid is urged against the resilient sealing material to reinforce the seal if there is an overpressure inside the collection vessel.

15. The kit of claim 1, wherein the mouthpiece module further comprises a seal configured to prevent air from flowing in the breath passageway at least through the mouthpiece breath inlet port when not in use.

16. The kit of claim 1, wherein the assembly comprises a cooling component configured to cool the collection vessel to a temperature below minus 60 degrees Celsius.

17. The kit of claim 1, wherein the mouthpiece module further comprises a mouthpiece configured to be in fluid communication with the mouthpiece breath inlet port when in use.

18. The kit of claim 1, wherein the mouthpiece module further comprises a saliva trap between the mouthpiece breath inlet port and the mouthpiece breath outlet port.

19. The kit of claim 1, wherein the collection vessel is configured to be centrifuge resistant and shaped to cause exhaled breath condensate to collect at a bottom of the chamber during centrifuging.

20. The kit of claim 1, wherein the collection vessel further comprises an extraction port for removal of the exhaled breath condensate from the collection vessel.

21. The kit of claim 20, wherein the extraction port is configured to be coupleable to a receptacle and wherein an overpressure in the collection vessel causes the exhaled breath condensate collected adjacent the extraction port to be ejected from the collection vessel and into a coupled receptacle.

22. The kit of claim 1, wherein the collection vessel further comprises a sealed vessel exhaust outlet to emit collected breath in use, and wherein the mouthpiece module further comprises an exhaust passageway coupled to a mouthpiece exhaust inlet port to conduct exhausted breath away from the collection vessel in use, and wherein the mouthpiece exhaust inlet port is moveable to cause the vessel exhaust outlet to become unsealed on or following insertion of the collection vessel into the assembly, and wherein the resealing mechanism comprises a sliding lid that covers and seals at least the vessel breath inlet and the vessel exhaust outlet when the resealing mechanism is in a sealed configuration.

23. The kit of claim 10, wherein the sliding lid of the resealing mechanism is urged open upon insertion into the assembly by a lip of the sliding lid that catches on the assembly.

24. The kit of claim 11, wherein the sliding lid of the resealing mechanism is urged shut upon removal from the assembly by a lip of the sliding lid that catches on the assembly.

25. The kit of claim 20, wherein the extraction port is arranged at a location of the chamber at which the exhaled breath condensate collects during centrifuging.

* * * * *